(12) United States Patent
Caillat et al.

(10) Patent No.: US 9,642,602 B2
(45) Date of Patent: May 9, 2017

(54) DEVICE FOR TRANSIENTLY CONTACTING AT LEAST ONE UNIT FOR CAPTURING BIOLOGICAL TARGETS WITH A FLUID CONTAINING THEM, METHOD FOR RECOVERING THE CAPTURED TARGETS AND SYSTEM FOR CONTACTING AND RECOVERY

(75) Inventors: Patrice Caillat, Grenoble (FR); François Berger, Meylan (FR); Raymond Campagnolo, Grenoble (FR); Marie-Line Cosnier, Grenoble (FR); Affif Zaccaria, Le Pont de Claix (FR)

(73) Assignees: Commissariat a l'Energie Atomique et aux Energies Alternatives, Paris (FR); Institut National de la Sante Et de la Recherche Medicale (INSERM), Paris (FR); Centre Hospitalier Universitaire De Grenoble, Grenoble (FR); Universite Jospeh Fourier, Grenoble (FR)

( * ) Notice: Subject to any disclaimer, the term of this patent is extended or adjusted under 35 U.S.C. 154(b) by 1089 days.

(21) Appl. No.: 13/521,632

(22) PCT Filed: Jan. 10, 2011

(86) PCT No.: PCT/IB2011/050087
§ 371 (c)(1),
(2), (4) Date: Dec. 12, 2012

(87) PCT Pub. No.: WO2011/086486
PCT Pub. Date: Jul. 21, 2011

(65) Prior Publication Data
US 2013/0079663 A1 Mar. 28, 2013

(30) Foreign Application Priority Data
Jan. 14, 2010 (FR) ...................................... 10 00136

(51) Int. Cl.
*A61B 10/02* (2006.01)
*A61B 10/00* (2006.01)

(52) U.S. Cl.
CPC .......... *A61B 10/02* (2013.01); *A61B 10/0045* (2013.01)

(58) Field of Classification Search
CPC ................................ A61B 10/0045–2010/008
See application file for complete search history.

(56) References Cited

U.S. PATENT DOCUMENTS 5,298,570 A * 3/1994 Tahara .................... C02F 1/681
523/124
6,063,029 A * 5/2000 Saita .................. A61B 10/0035
600/309

(Continued)

FOREIGN PATENT DOCUMENTS

WO    WO 94/14062 A1    6/1994

OTHER PUBLICATIONS

International Search Report and Written Opinion for Application No. PCT/IB2011/050087 dated May 17, 2011.

(Continued)

*Primary Examiner* — Michael C Stout
(74) *Attorney, Agent, or Firm* — Alston & Bird LLP

(57) ABSTRACT

The invention relates to a device for transiently contacting at least one unit for capturing biological targets with a body fluid containing them, a method for recovering the captured targets for analysis, and a system for contacting and recovering a capture substrate included in said unit. The invention relates to samples obtained in particular in vivo from body fluids of the human body, e.g. circulating body fluids, said fluids possibly containing, as targets, proteins, oligonucleotides such as RNA or DNA, antibodies, enzymes or cells. A contacting device (1) according to the invention com- (Continued)

prises: —a sampling tip (2) having a contacting end intended to be introduced into a medium containing said fluid, and—the or each capturing unit which is bound to said end and which comprises a capture substrate (3) defining a target capturing surface covered with at least one biocompatible and porous crosslinked polymer layer (4) designed to retain the or each capture substrate and only to allow biological particles including targets smaller than a limiting size to pass through, in such a way that the or each capture substrate is recoverable after said contacting by dissolution of the or each layer.

14 Claims, 1 Drawing Sheet

(56) References Cited

U.S. PATENT DOCUMENTS

| | | | | |
|---|---|---|---|---|
| 6,537,243 | B1* | 3/2003 | Henning | A61B 5/1411 |
| | | | | 600/581 |
| 7,927,548 | B2* | 4/2011 | Slowey | A61B 10/0051 |
| | | | | 422/422 |
| 2002/0188222 | A1* | 12/2002 | Saint-Ramon | A61D 19/024 |
| | | | | 600/573 |
| 2004/0153040 | A1* | 8/2004 | Martineau | A61K 9/7023 |
| | | | | 604/304 |
| 2004/0157951 | A1 | 8/2004 | Wolf | |
| 2006/0160064 | A1 | 7/2006 | Carbonell | |
| 2007/0122829 | A1* | 5/2007 | Ballerstadt | G01N 21/78 |
| | | | | 435/6.16 |
| 2007/0244368 | A1* | 10/2007 | Bayloff | A61B 10/0045 |
| | | | | 600/300 |
| 2007/0249961 | A1* | 10/2007 | Morrison | A61B 10/0045 |
| | | | | 600/572 |
| 2007/0255175 | A1* | 11/2007 | Sangha | A61B 10/0045 |
| | | | | 600/572 |
| 2010/0009456 | A1* | 1/2010 | Prins | G01N 33/558 |
| | | | | 436/164 |
| 2010/0045267 | A1* | 2/2010 | Dittmer | G01N 27/745 |
| | | | | 324/204 |
| 2010/0172797 | A1* | 7/2010 | Gould | A61B 5/14546 |
| | | | | 422/400 |
| 2011/0004122 | A1* | 1/2011 | Sangha | A61B 10/0045 |
| | | | | 600/572 |
| 2011/0034787 | A1* | 2/2011 | Hagino | A61B 5/14514 |
| | | | | 600/316 |
| 2011/0160798 | A1* | 6/2011 | Ackermann, Jr. | A61N 1/0551 |
| | | | | 607/46 |
| 2011/0270127 | A1* | 11/2011 | Vered | A61B 10/0096 |
| | | | | 600/573 |

OTHER PUBLICATIONS

Daniel, K. D. et al., *Lab on a Chip*, vol. 7 (2007).
Communication under Rule 71(3) of Intention to Grant Patent for European Patent Application No. 11 703 031.2 dated Oct. 17, 2014, 7 pages.

* cited by examiner

DEVICE FOR TRANSIENTLY CONTACTING AT LEAST ONE UNIT FOR CAPTURING BIOLOGICAL TARGETS WITH A FLUID CONTAINING THEM, METHOD FOR RECOVERING THE CAPTURED TARGETS AND SYSTEM FOR CONTACTING AND RECOVERY

FIELD

The present invention relates to a device for transiently contacting at least one unit for capturing biological targets with a body fluid containing them, a method for recovering these captured targets for analysis, and a system for performing this transient contacting and recovery of a capture substrate included in the or each capturing unit. The invention relates to samples obtained in particular in vivo from body fluids from the human body, for example circulating body fluids, and notably the blood, the cerebrospinal fluid, the interstitial fluid or the lymph, and said fluids can contain, as targets, proteins, oligonucleotides such as RNA or DNA, antibodies, enzymes or cells, as non-limiting examples.

BACKGROUND

Over many years, analytical techniques, whether based on genomics, proteomics or immunology, have progressed and have attained remarkable levels of sensitivity. These techniques are based on the recognition of elements of interest or biological targets, which must be extracted from the other elements present in the sample, whether it is obtained in vivo or ex vivo. If the target is absent or is at a level that is too low relative to the sensitivity of the method of analysis, measurement will not be possible.

The methods of sample preparation aim to capture the required targets and bring them in contact, after concentration, with a functionalized surface, on which a measurement is performed. They are very interesting as they make it possible, by concentrating said target, to relax the constraint on the sensitivity of measurement. In contrast, they are ineffective if the target is not present in the sample obtained. This drawback is evident, for example, during blood analysis, where the trend towards reduction of the sample volume has been adversely affected by the presence or absence of the element being sought and by the sensitivity of the measurement system.

A conventional method is the mixing of nanoparticles bearing recognition sites, such as nanobeads, with the sample containing the target and then carrying out recognition in bulk and finally recovering these nanoparticles by centrifugation or magnetic attraction before performing a controlled salting-out of the targets captured on a measurement surface.

Another known method consists of re-circulating the fluid to be tested over a surface that has the recognition sites in question.

The problems in testing body fluids circulating in the human body can be understood similarly. In the example where the volume to be tested is all of the blood or cerebrospinal fluid, by analogy it is possible to envisage the same approach, which consists of injecting metallic and/or magnetic nanoparticles into the body fluid or under the skin, leaving them to recognize the targets and then recovering them for example by application of a local magnetic field or by filtration in an extracorporeal circuit. This approach requires a very thorough investigation of the particles injected with respect to toxicity and filtration in the kidneys, the liver, etc. A problem that has still not been solved is satisfactory recovery of the injected particles.

To counter these problems and notably the risk of triggering immune reactions and toxicity reactions that can arise when said nanoparticles are injected into the human body, the solutions developed to date are generally based on encapsulation of these metallic and/or magnetic nanoparticles in various materials and in particular in biocompatible polymers. Depending on the porosity of said polymer, it can act as a filter, blocking biological species exceeding a certain size. In this context, "biological species" means cells, molecules, viruses, bacteria or antibodies.

In the article "Multi-reservoir device for detecting a soluble cancer biomarker", K. D. Daniel et al., Lab on a Chip, 2007, Vol. 7, the authors use magnetic iron oxide nanoparticles functionalized with antibodies for binding specifically to targets. To overcome a problem of instability, these nanoparticles are placed in wells of PDMS behind a polycarbonate membrane with pores of 10 nm. The biomarkers can pass through the membrane but the nanoparticles cannot, and therefore remain encapsulated. Detection is performed directly in the device by fluorescence.

Patent document US-A1-2007/0122829 describes a device for measuring the concentration of an analyte in a fluid by means of a detecting agent of the type of a macroporous polymer substrate matrix coupled to a ligand, within an at least partially permeable housing.

For its part, patent document US-A1-2004/0157951 discloses a measuring device comprising, on the one hand, a core for example of the hydrogel type, which can contain an agent capable of binding reversibly to an analyte and, on the other hand, a polymer coating with selective permeability. Detection is performed in situ by measurement of fluorescence.

In these known devices, the use of a coating or of encapsulation improves the performance of the measuring device either with respect to the efficiency of contrast, tolerance to the tissues or the capture capacity.

However, a major drawback of these known devices is that they are not designed for recovering the nanoparticles, such as nanobeads or nanospheres, after they are brought in contact with the required targets in the fluid in question, notably for capturing these targets or for analysis by MRI (magnetic resonance imaging). In other words, the problem of what becomes of the nanoparticles injected in vivo is not really tackled in the prior art.

SUMMARY

One aim of the present invention is to propose a device for transient contacting, notably in vivo, of at least one unit for capturing targets or biological species to be analysed with a body fluid containing said targets, which overcomes the aforementioned drawbacks.

For this purpose, a device according to the invention comprises:
 a sampling tip having a contacting end that is intended to be introduced into a medium containing this fluid, and
 said or each capturing unit that is bound to said end and which comprises a capture substrate defining a target capturing surface covered with at least one biocompatible, porous crosslinked polymer layer designed to retain said or each capture substrate and only allow biological particles to pass through, including those targets smaller than a limiting size, in such a way that the or each capture substrate, notably when it is bound to the targets, is recoverable after this contacting by dissolution of the or each layer.

"Capturing unit" means a substrate for capturing these targets having a capturing surface that is preferably functionalized and is covered with the or each aforementioned polymer layer. This dedicated surface for capturing the targets thus preferably contains functional groups designed to interact selectively or non-selectively with these targets in order to capture them.

The capturing surface that characterizes said or each capturing unit can be the surface of a polymer, semiconductor, metal or glass substrate, on which these functional groups have been grafted. This surface can be flat, micro- or nanostructured, or spherical. It can notably be the whole surface of nanoparticles of materials such as polystyrene, silica or a metal. These nanoparticles can be magnetic.

The expression "retain the or each capture substrate" means preventing all or part of this/these substrate(s) being dispersed in the organism. It is therefore a matter of keeping the capturing substrate(s) integral with the sampling tip.

"Sampling tip" means, in the present description, a tip, which can correspond to the end of a needle, of a catheter or of an external system that is able to be introduced into the medium containing the body fluid. Such a medium can for example be the vein of a human being or of an animal.

It should be noted that the or each crosslinked (i.e. gelled) polymer layer according to the invention thus has selective permeability, which makes it possible to ensure that during said contacting, these compounds are isolated from the elements of the fluid larger than said limiting size.

It should also be noted that this polymer coating layer that is porous to the compounds makes it possible:
  to avoid direct contact between the capture substrate that it covers—and notably the surface-grafted functional groups—and the body fluid, in order to prevent an immune reaction;
  to prevent diffusion of all or part of the or of each capture substrate in the medium; and
  for biological targets to be captured selectively according to their size.

Moreover, this polymer layer offers the advantage of imposing less mechanical stress on the surrounding biological tissues because of its flexibility.

According to another characteristic of the invention, the capturing surface of said or each capture substrate can be constituted of a part of the surface of the tip and/or can be connected to this tip, said surface preferably being functionalized by grafted functional groups that are designed to interact with said targets in order to capture them.

When the or each capture substrate constitutes a part of the tip, it is preferably located at said end of said tip, in the form of a functionalized surface covered with the polymer layer, and this surface can be a part of the surface of the tip or the surface of particles (preferably nanoparticles) embedded in the polymer layer, which covers a part of the surface of the tip.

When the or each capture substrate is connected to the tip, it can have the form of threads or of spheres, with diameters in the micrometre or nanometre range, which are kept integral with said tip, as will be explained in detail later.

The functional groups grafted on the surface of the or of each substrate and capable of capturing the targets form recognition sites of these targets, these groups preferably being selected from the group consisting of anionic functions, cationic functions, antibodies, and oligonucleotides such as aptamers. We may also mention the surface functions of the chromatography type and the functions of peptide and oligonucleotide libraries. Even more preferably, these functional groups that functionalize the or each capturing surface are charged groups of the anionic or cationic type.

Advantageously, said or each polymer layer can have a porosity that defines said limiting size, which is between 30 nm and 500 nm. When the or each capture substrate is constituted of spherical nanoparticles, the porosity of the polymer layer is defined to prevent these nanoparticles leaving this layer. It will thus be noted that a device according to the invention makes it possible:
  to leave the capture surfaces in close contact transiently with the circulating elements of the fluid and notably with the targets to be captured,
  for the functional groups bound to the targets to be easily recoverable via the reversible nature of the crosslinking (i.e. gelation) of said or each layer,
  to guarantee that these functional groups or any other part of the capture substrate are not dispersed in the fluid tested,
  to prevent adsorption of undesirable biological components of the fluid on these functional groups, said undesirable components typically being larger than the pore size and being for example blood cells such as red blood cells, or large proteins such as albumin, because of the filtration produced by said or each porous polymer layer.

Preferably, the device is designed so that the or each capturing unit, i.e. a capture substrate covered with at least one polymer layer, is protected mechanically during introduction in and withdrawal from the medium containing the biological fluid, and so that it can be deployed once said introduction has been performed. This mechanical protection has the aim of limiting the risks of dispersion of all or part of the capture substrate or capture substrates, for example on contact with the tissues during introduction and withdrawal of the device in an organism. Deployment permits exposure of the capturing system to the various species contained in the biological fluid.

For example, during introduction, the sampling tip and the or each capturing unit integral with this tip can be inserted in a protective guide sheath, then deployed when the end of this protective sheath has been introduced into said medium. Preferably, deployment is envisaged to be reversible, and permits return to a folded-back position prior to withdrawal of the sheath from said medium. The protective sheath can be in the form of a hollow end of a tube, of a needle, or of a catheter, provided that the tip and/or the or each capturing unit can be translated inside said end, so as to be deployed or folded back depending on the direction of translation.

According to a first embodiment of the invention, said or each polymer layer covers a defined zone, for example metallic, of the wall of the tip, which is preferably of the needle or catheter type. Thus, according to this first embodiment, the capture substrate is the part of the tip whose surface is preferably functionalized and covered with said or with each polymer layer.

Advantageously according to this first embodiment of the invention, the capturing surface of said or each capture substrate defines at least one functionalized surface of the tip, which can be defined:
  (i) by said wall zone of the tip before it is covered by said or each layer, and/or
  (ii) by respective functionalized surfaces of particles embedded in said or each layer.

According to said case (i), the capturing surface of said or each capture substrate can be formed exclusively or partly from said functional groups that are formed on the surface directly on said wall zone of the tip (and said wall is thus functionalized) and covered with said porous polymer layer. Said wall zone is then advantageously constituted of a material that is chemically functionalizable and moreover structurable, such as silicon, glass, a metallic material or an oxide, or a polymer.

According to said case (ii), said or each capture substrate can be constituted exclusively or partly of said surface-functionalized particles that are embedded in said or each layer, these particles being of the magnetic or non-magnetic type and preferably being nanobeads or nanospheres made of a ferromagnetic material such as an iron oxide and with an average size between 50 nm and 250 nm.

In relation to said first embodiment of the invention, the material of said wall zone of the tip can advantageously have a geometric surface structuring for optimizing adhesion and good conformation of said or each polymer layer. Moreover, this defined zone of the tip can advantageously form a dish, a groove or a slit, so as to facilitate adhesion of said or each layer on this zone of the tip.

According to a second embodiment of the invention, said or each capturing unit is connected to said contacting end of the tip via connecting means that are fixed to said end for example by welding or gluing.

According to a first example of this second embodiment of the invention, said connecting means comprise a biocompatible porous bag that is fixed to said end of the tip and that envelops said or each capturing unit, for example approximately spherical (the porosity of said bag preferably being of the order of a µm, or even less than 1 µm), and said unit contains particles that constitute said substrate and that are embedded in said or each polymer layer. In this case, the or each capturing unit has a dimension larger than the porosity of the bag (dimension of the capturing unit means the diameter or the greatest width of the capture substrate covered with the corresponding polymer layer).

In this first example, said porous bag can advantageously envelop a plurality of said capturing units, which can for example each comprise a capture substrate in the form of particles, which are of the magnetic or non-magnetic type and are preferably nanobeads or nanospheres made of a ferromagnetic material such as an iron oxide, said particles having an average size preferably between 50 nm and 250 nm, said particles being covered with said or each porous polymer layer.

According to a second example of this second embodiment of the invention, said connecting means comprise at least one biocompatible thread that is fixed to said end of the tip and that directly or indirectly bears said or each capturing unit, which has at least one functionalized capturing surface defined by this thread and/or by the surfaces of particles embedded in said or each polymer layer that is formed on this thread.

In this second example, said or each capture substrate can be constituted exclusively or partly:
of said functional groups that are formed on the surface of said or each thread (which is thus functionalized) and that are covered with a porous polymer coating or sheath for this thread forming said layer or, as a variant,
of said particles that are embedded in a porous polymer coating or sheath for said or each thread forming said layer, these particles being of the magnetic or non-magnetic type and preferably being nanobeads or nanospheres of a ferromagnetic material such as an iron oxide, said particles having an average size preferably between 50 nm and 250 nm. The surfaces of these nanoparticles are functionalized.

In another variant relating to this second example, said or each thread can carry indirectly at least one capture substrate, which is for example approximately spherical. Advantageously, said connecting means can then comprise a plurality of these threads, each bearing several capturing units, which can be formed at the contact of each thread by dipping. According to this variant, each thread can thus bear a plurality of capturing units aligned along this thread.

According to a third example of this embodiment, the capture substrates are integrated with a meshed structure composed of a plurality of strands or segments organized according to a network defining meshes, the size of which varies between 30 and 100 µm and is preferably of about 50 µm. Said mesh can be of polygonal or circular section, and the strands defining the mesh are connected to the tip, directly or via a thread. These strands can be made of metal or of polymer(s), and they are covered with a porous polymer layer encapsulating functionalized nanoparticles. These strands can also be functionalized, and covered with a porous polymer layer.

A meshed structure of this kind is initially folded up in a guide structure, for example tubular, during introduction into the biological medium, then it is deployed according to known means, for example by deployment means used for stents. The mesh structure is then folded-up in the guide structure before being withdrawn from the medium.

In these examples and variants, the device according to the invention can permit deployment of the or each capturing unit in the body fluid being analysed. For example, the capturing units are assembled in a hollow guide sheath forming for example the hollow end of a needle, of a catheter or of a tube, during introduction and withdrawal of this sheath in the medium containing the body fluid. When the sheath has entered the medium, the or each capturing unit can be deployed, and said deployment can for example be effected by translation of the or each capturing unit within this guide sheath. Withdrawal is effected by a translation in the reverse direction, so that the or each capturing unit can be accommodated in this hollow sheath.

According to another characteristic of the invention, the or each layer is based on at least one biocompatible polymer with reversible gelation preferably selected from the group consisting of alginate gels (for example alginate hydrogels), copolymers of alginate and poly-L-lysine, chitosan, agarose, cellulose, poly(trimethylammonium ethylacrylate methyl sulphate)-b-poly(acrylamide), poly(hydroxyethylmethacrylate) (HEMA), poly(hydroxyethylmethacrylate-methyl ethacrylate) (HEMA-MMA) and other copolymers derived from methacrylate, polyethylene glycols, copolymers of acrylonitrile and polyethylene glycol, polysaccharides and mixtures thereof.

Even more preferably, said or each layer is based on at least one alginate gel that is obtained by means of polycations preferably selected from the group consisting of polycations of calcium, barium, iron and strontium.

The use of an alginate is in fact particularly advantageous, because it is perfectly biocompatible, non-toxic and allows the targets that are to be captured to pass through it. Moreover, it is capable of being polymerized and gelled (or crosslinked) at ambient temperatures and remains in the gelled form at body temperatures and at pH corresponding to physiological conditions.

According to another aspect of the invention, a system for transiently contacting at least one unit for capturing biological targets with a body fluid containing said targets, and for recovering a capture substrate included in the or each capturing unit, comprises a device for transient contacting such as that mentioned above and further comprises:

- means for dissolving said or each layer after said contacting, to provide access to said or each capture substrate that is embedded therein and that is bound or is not bound to said targets to be analysed, said dissolving means comprising at least one chelating agent of said polycations, which is, for example for sodium polycations, ethylenediamine tetraacetic acid (EDTA) or sodium citrate, and
- means for recovery, preferably magnetic, of said or each capture substrate, in the case when said substrate is constituted of magnetic particles with functionalized respective surfaces.

A method of recovery, according to the invention, of biological targets previously captured by a contacting device as defined above, notably by grafting of said targets onto the capturing surface of said or each capturing unit, comprises the following successive stages:

- washing of the or each capturing unit bound to said end of the tip by a buffer solution, preferably saline,
- dissolving the or each polymer layer covering said or each capture substrate, preferably by at least one chelating agent of polycations such as ethylenediamine tetraacetic acid (EDTA) in the preferred case when said layer is based on an alginate gel, then
- analysis of the biological targets present on the capturing surface of the or of each capture substrate.

BRIEF DESCRIPTION OF THE DRAWINGS

Other advantages, characteristics and details of the invention will become clear from the rest of the description that follows, referring to the appended drawings, given solely as examples, and in which.

DETAILED DESCRIPTION

In the examples described below, an alginate hydrogel formed by polymerization in a suitable aqueous buffer composed of 150 mM of NaCl and 10 mM of HEPES at pH 7.4 was used for the or each porous polymer layer. The alginate was mixed with this buffer at a ratio from 0.25% to 2%, preferably around 1%, to obtain said polymer layer in which the or each capture substrate according to the invention, with advantageously functionalized capturing surface, for binding to the biological targets of the fluid, is embedded.

Then gelation (i.e. crosslinking) of this layer of alginate was performed by contacting the polymer thus formed with an aqueous bath containing polycations, preferably calcium (it being understood that barium, iron or strontium cations can also be used). This bath contained from 10 mM to 1 M of $CaCl_2$, preferably 100 mM of $CaCl_2$. The porosity of the crosslinked layer of alginate means that undesirable components of the fluid of larger size are excluded. These undesirable components can be blood cells and large proteins, such as albumin or immunoglobulin.

Figure 2:
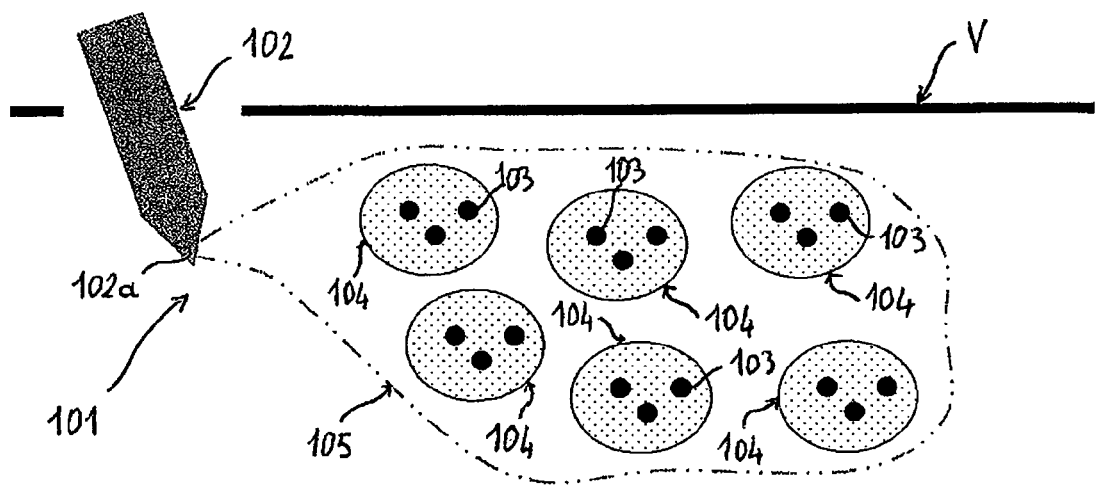
FIG. 2 is a schematic sectional view of a contacting device according to said first example of said second embodiment of the invention of the type with a porous bag connected to a tip.
Figure 3:
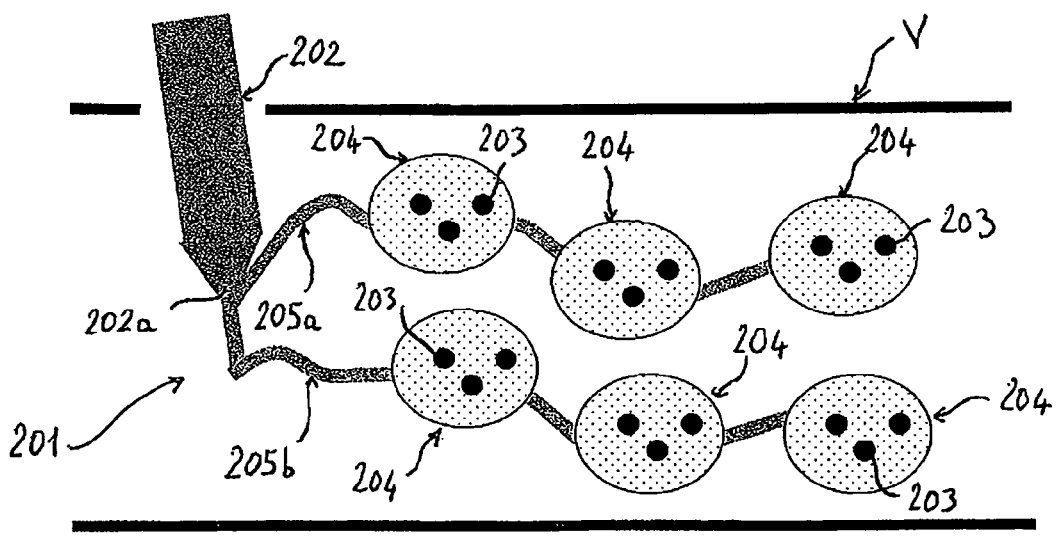
FIG. 3 is a schematic sectional view of a contacting device according to said second example of said second embodiment of the invention of the type with threads connected to a tip.

Referring to FIGS. 2 and 3, for example a microsystem for ejection of droplets was used for forming approximately spherical polymer layers with diameter from 10 µm to 50 µm, said microsystem having the required dimensions that are known per se.

A commercially available ejector (preferably with a piezoelectric tip) can also be used for forming said spherical layers with a diameter from 50 µm to 600 µm.

Figure 1:
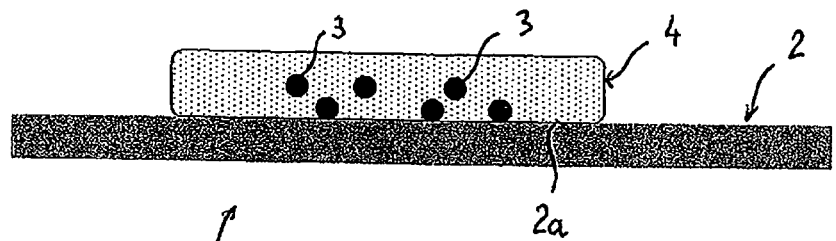
FIG. 1 is a schematic view in longitudinal section of a contacting device of the catheter type according to said first embodiment of the invention.

Once the targets had been captured by the capture substrate formed from particles embedded in the layer of FIG. 1 or in each layer of FIGS. 2 and 3, the capture substrate enclosed in the or each layer was recovered by effecting a "degelation" or dissolution of said layer by bringing it into contact with a chelator of the polycations used, which is advantageously constituted of EDTA or of sodium citrate in the case of calcium polycations.

Once the or each layer had been "degelled", the capture substrate that was embedded therein was recovered for example using a magnet for "depositing" it in a well, in the preferred case when the substrates embedded in the spherical layers of FIGS. 2 and 3 were each formed of nanomagnetic particles.

The method according to the invention for recovery of the biological targets captured by these capture substrates comprises the following successive stages:

- washing the or each capturing unit in a buffer solution, preferably a saline buffer of the PBS type (Phosphate Buffered Saline);
- depolymerization, using for example a solution of EDTA (ethylenediamine tetraacetic acid) at 0.5 M;
- analysis of the biological targets surface-grafted on the capture substrates (this analysis can be performed by any technique for identification of bio-markers grafted on the surface of a substrate known by a person skilled in the art, notably a mass spectrometry technique, for example SELDI (Surface Enhanced Laser Desorption/Ionization).

The contacting device 1 depicted in FIG. 1 is essentially constituted of a tip 2 of the catheter tip type which is designed to be introduced into a vein or biological cavity of a human being or an animal, to be left in place for a few minutes, and then withdrawn. This tip 2 can be made of an organic material (for example plastic) or an inorganic material (for example metallic) and more generally of any material that can constitute a tip of a catheter or of a needle for injection or for taking samples.

In the example in FIG. 1, which is according to the aforementioned case (ii), the functional groups defining recognition sites of the targets are constituted of surface-functionalized nanoparticles 3, which are embedded in a polymer layer 4 coated on the zone of wall 2a of the tip 2 and which are constituted of nanobeads or nanospheres made of a ferromagnetic iron oxide and having an average size for example of about 100 nm. The nanoparticles of this kind marketed by the companies ChemiCell or Biorad were used, employing combinatorial library technology. In this example, the capture substrate is formed by the nanoparticles 3, and the corresponding capturing unit is constituted of the polymer layer 4 and the nanoparticles 3 embedded in this layer.

The layer 4, which is preferably based on crosslinked alginate as defined above, was deposited as a thin layer on this wall of the tip 2a, for example metallic, coating a plurality of these nanoparticles 3 (typically from several tens of thousands to several billion) by polymerization and gelation in situ of the alginate coating these nanoparticles 3.

Advantageously, the zone of wall 2a of the tip 2 intended to receive this layer of alginate 4 is in the shape of a dish or groove, permitting gelation to be performed there directly and easily, and facilitating adhesion of this layer. The groove can be made along an axis parallel to the longitudinal axis of the tip, its depth being between 300 μm and 1 mm. As a variant, this polymer layer 4 could be formed on tip 2 by dipping in suitable solutions.

It is possible, moreover, to provide prior functionalization of wall 2a of the tip 2 preferably with cationic charged functions (poly-Lysine, amine, ammonium, polymethylene-co-guanidine, poly-ornithine), or as a variant with those previously mentioned in the general description of the invention, to give better adhesion of the polymer layer 4 of alginate on this wall 2a.

Following withdrawal of this tip 2 from the vein or biological cavity, as explained above, "degelation" of this layer 4 is then carried out, in order to recover the nanoparticles 3 bound to the targets of the fluid for analysis.

The contacting device 101 illustrated in FIG. 2 comprises, in addition to a tip 102 for example of the catheter type intended to penetrate into a vein V or biological cavity of a human being or of an animal, a plurality of approximately spherical polymer layers 104 each containing a plurality of nanoparticles 103 for example like those described with reference to FIG. 1 and which are connected to the tip 102 by a biocompatible porous bag 105 fixed (for example by welding or gluing) to the end 102a of the tip 102 intended to be embedded in the fluid. Bag 105, like a dialysis bag but porous with pores of controlled size, is for example made of Nylon, of polycarbonate or of some other biocompatible polymer, or even of cellulose. The porosity of this bag 105 is preferably selected to be of the order of 1 μm, or even several μm, like that of the spherical layers of alginate 104. In this example, the capture substrates are each formed of nanoparticles 103 and each capturing unit is formed of a polymer layer 104 in which these nanoparticles 103 are embedded.

As for the diameter or smallest transverse dimension of each of the spherical layers of alginate 104 embedded in bag 105, it is preferably greater than several μm, which makes it possible to use a bag 105 with porosity of the order of 1 μm, or even of several μm, so that it is relatively easy to make this bag 105.

Advantageously, gelation of the spherical layers 104 in which the nanoparticles 103 are embedded is performed directly in the bag by injecting drops of alginate into it, said bag 105 containing the gelling agent beforehand. The liquid containing this gelling agent is then replaced with a physiological buffer, utilizing the presence of pores, for use in viva As mentioned previously, the use of a reversible alginate means that the nanoparticles 103 bound to the required targets can easily be recovered for subsequent analyses, after withdrawing bag 105 from the vein V or the biological cavity.

The contacting device 201 illustrated in FIG. 3 comprises, in addition to a tip 202 for example formed by an end of a catheter intended to penetrate into a vein V or biological cavity of a human being or an animal, a plurality of approximately spherical polymer layers 204 each containing a plurality of nanoparticles 203 for example such as those described with reference to FIG. 1 and which are connected to the tip 202 by at least one biocompatible thread 205a, 205b bearing these layers 204 and fixed (for example by welding or gluing) to the end 202a of the tip 202 intended to be embedded in the fluid. In the example in FIG. 3, several of these threads 205a, 205b each carry a plurality of these layers 204, which are directly formed with spacing in contact with each thread 205a, 205b by dipping in suitable solutions. In this example, the capture substrates are each formed of nanoparticles 203, and each capturing unit comprises a polymer layer 204 in which these nanoparticles 203 are embedded.

These threads 205a, 205b are made of any biocompatible material that can be formed into a thread (e.g. of Nylon or some other polymer, or even of cellulose, as non-limiting examples). Advantageously, threads 205a, 205b that have previously been surface-functionalized are used, to provide better adhesion of the polymer layer of alginate 204 on the surface of each thread 205a, 205b, the functionalizations that are possible being of the same type as those mentioned above with reference to FIG. 1.

To form these alginate-based spherical layers 204 in contact with the threads 205a, 205b, the latter are introduced into a gelling bath and the droplets of alginate are formed directly on these threads 205a, 205b by directed ejection.

As previously, after these threads 205a, 205b bearing the nanoparticles 203 embedded in the layers of alginate 204 have been left in place for some minutes in the vein V or biological cavity via the tip 202 that carries them, this tip 202 is withdrawn from the fluid and then, as explained above, "degelation" of each spherical layer of alginate 204 is performed in order to recover the nanoparticles 203 bound to the targets of the fluid for analysis.

The invention claimed is:

1. A device for transient contacting notably in vivo of an one unit for capturing biological targets with a body fluid containing said targets, said device comprising:
    a sampling tip having a contacting end configured to be introduced into a medium containing said fluid, and
    said capturing unit, which is bound to said contacting end and which comprises a capture substrate defining a target capturing surface covered with a biocompatible and porous crosslinked polymer layer configured to retain said capture substrate and only to allow biological particles including said targets smaller than a limiting size to pass through, in such a way that said capture substrate is recoverable after this contacting by dissolution of said polymer layer;
    wherein said capturing unit is connected to said contacting end of the tip via connecting means, which are fixed to said contacting end by welding or gluing, and said connecting means comprise a biocompatible porous bag which is fixed to said contacting end of the tip and which envelops said capturing unit, which contains particles that constitute said substrate and that are embedded in said polymer layer.

2. The device according to claim 1, wherein said capturing surface of said capture substrate is constituted of a part of the surface of the tip and/or is connected to said tip, said surface being functionalized by grafted functional groups which are designed to interact with said targets in order to capture them, these functional groups being selected from the group consisting of anionic functions, cationic functions, antibodies and oligonucleotides.

3. The device according to claim 1, wherein said polymer layer has a porosity defining said limiting size which is between 30 nm and 500 nm.

4. The device according to claim 1, wherein said or each polymer layer covers a defined zone of the wall of the tip, which is of the needle or catheter type.

5. The device according to claim 4, wherein said capturing surface of said capture substrate defines at least one functionalized surface of the tip which is defined:
- by said defined zone of the tip before it is covered by said polymer layer, and/or
- by the respective functionalized surfaces of particles embedded in said polymer layer.

6. The device according to claim 4, wherein said capturing surface of said capture substrate is constituted exclusively or partly of said functional groups that are formed on the surface directly on said defined zone of the functionalized wall of the tip and covered with said polymer layer.

7. The device according to claim 5, wherein said capture substrate is constituted exclusively or partly of said surface-functionalized particles which are embedded in said polymer layer, these particles being of the magnetic or non-magnetic type and being nanobeads or nanospheres made of a ferromagnetic material with an average size between 50 nm and 250 nm.

8. The device according to claim 4, wherein said defined zone of the wall of the tip forms a dish, a groove or a slit, so as to facilitate adhesion of said polymer layer directly on said defined zone of the tip.

9. The device according to claim 1, wherein said porous bag envelops a plurality of said capturing units of approximately spherical shape, each capturing unit of said comprising a capture substrate in the form of particles, which are of the magnetic or non-magnetic type and are nanobeads or nanospheres made of a ferromagnetic material, said particles having an average size between 50 nm and 250 nm.

10. The device according to claim 1, wherein said polymer layer is based on at least one biocompatible polymer with reversible gelation selected from the group consisting of alginate gels, copolymers of alginate and of poly-L-lysine, chitosan, agarose, cellulose, poly(trimethylammonium ethylacrylate methyl sulphate)-b-poly(acrylamide), poly(hydroxyethylmethacrylate) (HEMA), poly(hydroxyethylmethacrylate-methyl ethacrylate) (HEMA-MMA) and other copolymers based on methacrylate, polyethylene glycols, copolymers of acrylonitrile and of polyethylene glycol, polysaccharides and mixtures thereof.

11. The device according to claim 10, wherein said polymer layer is based on at least one alginate gel, which is gelled by means of polycations selected from the group consisting of polycations of calcium, barium, iron and strontium.

12. System for transient contacting of at least one unit for capturing biological targets with a body fluid containing these targets, and for recovering a capture substrate included in the or each capturing unit, wherein this system comprises a device for transient contacting according to claim 1 and further comprises:
- means for dissolving said polymer layer after said contacting, to provide access to said capture substrate that is embedded therein and that is bound or is not bound to said targets to be analysed, said dissolving means comprising at least one chelating agent of said polycations, which is for sodium polycations, ethylenediamine tetraacetic acid (EDTA) or sodium citrate, and
- means for recovery of said or each capture substrate, in the case when said substrate is constituted of magnetic particles with respective functionalized surfaces.

13. Method for recovery of biological targets previously captured by a contacting the device according to claim 1, notably by grafting of said targets onto the capturing surface of said capturing unit, wherein the method comprises the following successive stages:
- washing of the capturing unit bound to said contacting end of the tip with a buffer solution,
- dissolution of said polymer layer covering said or each capture substrate, then
- analysis of the biological targets present on the capturing surface of said or each capture substrate.

14. The method of claim 13, wherein said dissolution is performed by at least one chelating agent of polycations.

* * * * *